United States Patent [19]

Mieno et al.

[11] Patent Number: 4,819,602
[45] Date of Patent: Apr. 11, 1989

[54] SYSTEM OF ABNORMALITY DETECTION FOR OXYGEN CONCENTRATION SENSOR

[76] Inventors: Toshiyuki Mieno; Toyohei Nakajima; Yasushi Okada; Nobuyuki Oono, all of c/o Kabushiki Kaisha Honda, 4-1, Chuo 1-chome, Wako-City, Saitama, Japan

[21] Appl. No.: 30,494

[22] Filed: Mar. 27, 1987

[30] Foreign Application Priority Data

Mar. 27, 1986 [JP] Japan .................................. 61-69095

[51] Int. Cl.$^4$ ............................................. F02D 41/22
[52] U.S. Cl. .................................... 123/479; 123/489
[58] Field of Search ............... 123/440, 479, 489, 589; 60/276; 73/23; 204/406

[56] References Cited

U.S. PATENT DOCUMENTS 4,502,443  3/1985  Hasegawa et al. .................. 123/479

FOREIGN PATENT DOCUMENTS 54-151730  11/1979  Japan .................................... 123/489
59-96451   6/1984  Japan .................................... 123/440
60-98142   6/1985  Japan .................................... 123/440

Primary Examiner—Andrew M. Dolinar

[57] ABSTRACT

A system of abnormality detection for an oxygen concentration sensor employed to sense the oxygen concentration in engine exhaust gas, for obtaining data to control the air/fuel ratio of a fuel mixture supplied to the engine, the oxygen concentration sensor including a sensor cell element and an oxygen pump element. The system serves to detect an abnormality such as an open-circuit or a short-circuit in electrode connecting leads of the oxygen pump element, on the basis of a level of the sensed pump current together with an air/fuel ratio compensation value which is derived from a sensed oxygen concentration level.

3 Claims, 5 Drawing Sheets

SYSTEM OF ABNORMALITY DETECTION FOR OXYGEN CONCENTRATION SENSOR

BACKGROUND OF THE INVENTION

1. Field of the Invention

The present invention relates to a system of abnormality detection for an oxygen concentration sensor which senses the level of oxygen concentration in a gas such as engine exhaust gas.

2. Description of Background Information

In order to reduce exhaust gas pollutants and to improve the fuel consumption of an internal combustion engine, it is now common practice to employ an oxygen concentration sensor to detect the concentration of oxygen in the engine exhaust gas, and to execute feedback control of the air/fuel ratio of the mixture supplied to the engine such as to hold the air/fuel ratio at a target value. This feedback control is performed in accordance with an output signal from the oxygen concentration sensor.

One form of oxygen concentration sensor which can be employed for such air/fuel ratio control functions by producing an output signal which varies in level in accordance with the oxygen concentration in the engine exhaust gas. Such an oxygen concentration sensor has been disclosed for example in Japanese patent laid-open No. 52-72286. This sensor consists of an oxygen ion-conductive solid electrolytic member formed as a flat plate having a pair of electrodes formed on two main faces, with one of these electrode faces forming part of a gas holding chamber. The gas holding chamber communicates with a gas which is to be measured, i.e. exhaust gas, through a lead-in aperture. With such an oxygen concentration sensor, the oxygen ion-conductive solid electrolytic member and its electrodes function as an oxygen pump element. By passing a flow of current between the electrodes such that the electrode within the gas holding chamber becomes a negative electrode, oxygen gas within the gas holding chamber adjacent to this negative electrode becomes ionized, and flows through the solid electrolytic member towards the positive electrode, to be thereby emitted from that face of the sensor element as gaseous oxygen. The current flow between the electrodes is a boundary current value which is substantially constant, i.e. is substantially unaffected by variations in the applied voltage, and is proportional to the oxygen concentration within the gas under measurement. Thus, by sensing the level of this boundary current, it is possible to measure the oxygen concentration within the gas which is under measurement. However if such an oxygen concentration sensor is used to control the air/fuel ratio of the mixture supplied to an internal combustion engine, by measuring the oxygen concentration within the engine exhaust gas, it will only be possible to control the air/fuel ratio to a value which is in the lean region, relative to the stoichiometric air/fuel ratio. It is not possible to perform air/fuel ratio control to maintain a target air/fuel ratio which is set in the rich region. An oxygen concentration sensor which will provide an output signal level varying in proportion to the oxygen concentration in engine exhaust gas for both the lean region and the rich region of the air/fuel ratio has been proposed in Japanese patent laid-open No. 59-192955. This sensor consists of two oxygen ion-conductive solid electrolytic members each formed as a flat plate, and each provided with a pair of electrodes. Two opposing electrode faces, i.e. one face of each of the solid electrolytic members, form part of a gas holding chamber which communicates with a gas under measurement, via a lead-in aperture. The other electrode of one of the solid electrolytic members faces into the atmosphere. In this oxygen concentration sensor, one of the solid electrolytic members and a pair of electrodes functions as an oxygen concentration ratio sensor cell element. The other solid electrolytic member and a pair of electrodes functions as an oxygen pump element. If the voltage which is generated between the electrodes of the oxygen concentration ratio sensor cell element is higher than a reference voltage value, then current is supplied between the electrodes of the oxygen pump element such that oxygen ions flow through the oxygen pump element towards the electrode of that element which is within the gas holding chamber. If the voltage developed between the electrodes of the sensor cell element is lower than the reference voltage value, then a current is supplied between the electrodes of the oxygen pump element such that oxygen ions flow through that element towards the oxygen pump element electrode which is on the opposite side to the gas holding chamber. In this way, a value of current flow between the electrodes of the oxygen pump element is obtained which varies in proportion to the oxygen concentration of the gas under measurement, both in the rich and the lean regions of the air/fuel ratio.

However with such an oxygen concentration sensor, if an abnormality of the sensor should occur, then not only will it be impossible to achieve a desired oxygen concentration sensing characteristic, but it will be no longer possible to accurately control the air/fuel ratio, so that the effectiveness of exhaust gas pollution removal will be reduced. It is therefore desirable to provide a method of reliably detecting any abnormality of components of such an oxygen concentration sensor.

SUMMARY OF THE INVENTION

It is an objective of the present invention to provide a system of abnormality detection for an oxygen concentration sensor whereby an abnormality of a system of electrical connections of an oxygen pump element can be reliably detected.

A system of abnormality detection for an oxygen concentration sensor according to the present invention is characterized in that an abnormality of a system of electrical connections of electrodes of an oxygen pump element is detected based upon a level of pump current which flows between the electrodes of the oxygen pump element and upon an air/fuel ratio compensation value utilized to control the air/fuel ratio of a mixture supplied to an engine such as to maintain that ratio at a target air/fuel ratio.

The present invention provides a system of abnormality detection for an oxygen concentration sensor of an air/fuel ratio control apparatus of an internal combustion engine, the sensor comprising two pairs of electrodes disposed mutually opposing with each of the pairs, sandwiching an oxygen ion-conductive solid electrolytic member, gas diffusion control means for leading an exhaust gas of an internal combustion engine to the vicinity of on electrode of each of the two pairs of electrodes, control means for applying a pump voltage, determined in accordance with a voltage difference between a sensor voltage which is produced between a first pair of the two pairs of electrodes and a reference voltage, between a second pair of the two pairs of electrodes to maintain the sensor voltage at the reference voltage, the control means thereby producing as an output which represents an oxygen concentration sensing value, a value of pump current which flows between the second pair of electrodes, and means for deriving an air/fuel ratio compensation value in accordance with the oxygen concentration sensing value, for controlling an air/fuel ratio of a mixture supplied to the internal combustion engine such as to maintain the air/fuel ratio at a target air/fuel ratio, and drive means for driving an air/fuel ratio control means of the internal combustion engine in accordance with a corrected air/fuel ratio control value which is obtained by applying compensation to an air/fuel ratio control value in accordance with the air/fuel ratio compensation value, the method being characterized in that an abnormality of an electrical connection system of the second pair of electrodes is detected based upon the pump current and upon the air/fuel ratio compensation value.

DETAILED DESCRIPTION OF EMBODIMENTS

Figure 1:
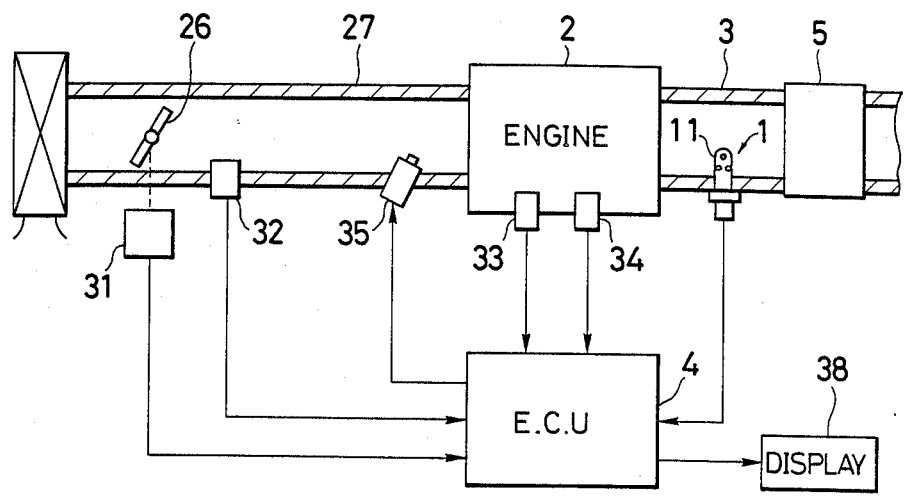
FIG. 1 is a diagram showing an electronic control fuel injection apparatus equipped with an oxygen concentration sensor, suitable for application of the abnormality detection system of the present invention.
Figure 2:
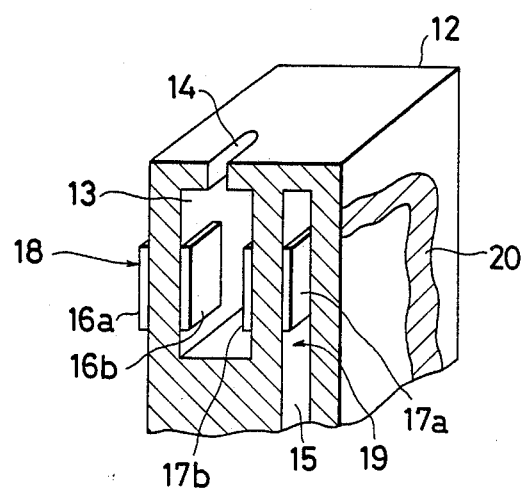
FIG. 2 is a diagram for illustrating the internal configuration of an oxygen concentration sensor detection unit.
Figure 3:
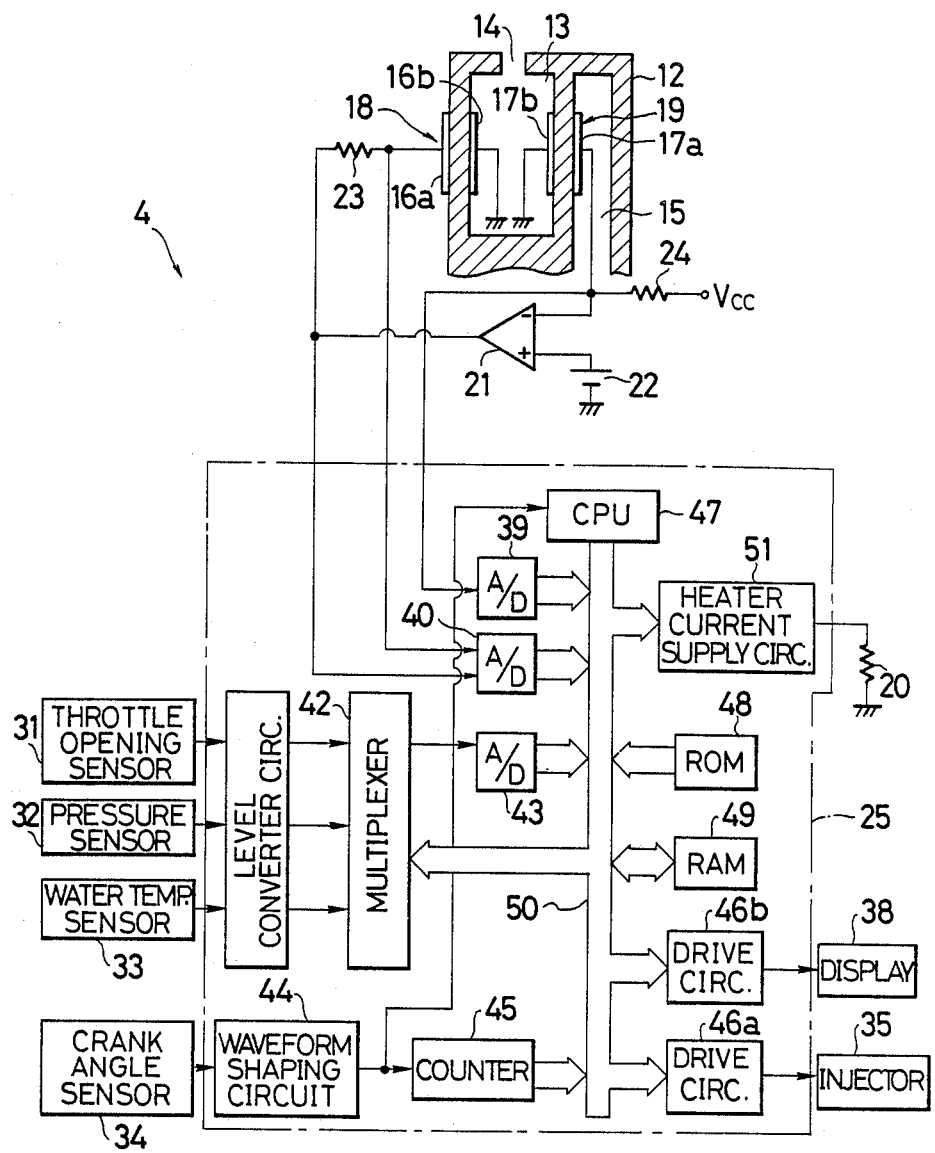
FIG. 3 is a block circuit diagram of the interior of an ECU (Electronic Control Unit)

An embodiment of the present invention will now be described, referring to the drawings. FIGS. 1 through 3 show an electronic fuel control apparatus for an internal combustion engine incorporating an oxygen concentration sensor which utilizes the output compensation method of the present invention. In this apparatus, an oxygen concentration sensor detection unit 1 is mounted within an exhaust pipe 3 of an engine 2, upstream from a catalytic converter 5. Inputs and outputs of the oxygen concentration sensor detection unit 1 are coupled to an ECU (Electronic Control Unit) 4.

The protective case 11 of the oxygen concentration sensor detection unit contains an oxygen ion-conductive solid electrolytic member 12 which may have, for example a substantially rectangular shape of the form shown in FIG. 2. A gas holding chamber 13 is formed in the interior of the solid electrolytic member 12, and communicates via a lead-in aperture 14 with exhaust gas at the exterior of solid electrolytic member 12, constituting a gas to be sampled. The lead-in aperture 14 is positioned such that the exhaust gas will readily flow from the interior of the exhaust pipe into the gas holding chamber 13. In addition, an atmospheric reference chamber 15 is formed within the solid electrolytic member 12, into which atmospheric air is led. The atmospheric reference chamber 15 is separated from the gas holding chamber 13 by a portion of the solid electrolytic member 12 serving as a partition. As shown, pairs of electrodes 17a, 17b and 16a, 16b are respectively formed on the partition between chambers 13 and 15 and on both sides of the wall of chamber 13 opposite to chamber 15. The solid electrolytic member 12 functions in conjunction with the electrodes 16a and 16b as an oxygen pump element 18, and functions in conjunction with electrodes 17a, 17b as a sensor cell element 19. A heater element 20 is mounted on the external surface of the atmospheric reference chamber 15.

The oxygen ion-conductive solid electrolytic member 12 can be formed, for example, of $ZrO_2$ (zirconium dioxide), while the electrodes 16a through 17b are each formed of platinum.

As shown in FIG. 3, ECU 4 includes an oxygen concentration sensor control section, consisting of a differential amplifier 21, a reference voltage source 22, and resistors 23 and 24. Electrode 16b of the oxygen pump element 18 and electrode 17b of sensor cell element 19 are each connected to ground potential, and electrode 17a of sensor cell element 19 is connected through resistor 24 to a supply voltage $V_{cc}$. Electrode 17a is also connected to an input terminal of the differential amplifier 21, which produces an output voltage in accordance with the difference between a voltage developed across electrodes 17a and 17b of the sensor cell element 19 and the output voltage from the reference voltage source 22. The output voltage from reference voltage source 22 is a value corresponding to a stoichiometric air/fuel ratio (for example 0.4 V). The output terminal of differential amplifier 21 is connected through current sensing resistor 23 to electrode 16a of the oxygen pump element 18. The terminals of current sensing resistor 23 constitute a pair of output terminals of the oxygen concentration sensor, and are coupled to a microcomputer which constitutes the control circuit 25.

A throttle valve opening sensor 31 which produces an output voltage in accordance with the degree of opening of throttle valve 26, and which can be implemented as a potentiometer, is coupled to control circuit 25, to which is also connected an absolute pressure sensor 32 which is mounted in intake pipe 27 at a position downstream from the throttle valve 26 and which produces an output voltage varying in level in accordance with the absolute pressure within the intake pipe 27. Control circuit 25 is also connected to a water temperature sensor 33 which produces an output voltage varying in level in accordance with the temperature of the engine cooling water, and to a crank angle sensor 34 which produces a signal consisting of successive pulses respectively produced in synchronism with rotation of the crankshaft (not shown in the drawings) of engine 2. Control circuit 25 is also connected to an injector 35, provided in the intake pipe 27, near the intake valves (not shown in the drawings) of engine 2.

Control circuit 25 includes an analog/digital (A/D) converter 39 for converting the voltage $V_S$ developed between electrodes 17a and 17b of sensor cell element 19 into a digital signal, and an A/D converter 40 receives the voltage developed across the current sensing resistor 23 as a differential input and converts that voltage to a digital signal. Control circuit 25 also includes a level converter circuit 41 which performs level conversion of each of the output signals from the throttle valve opening sensor 31, the absolute pressure sensor 32, and the water temperature sensor 33. The resultant level-converted signals from level converter circuit 41 are supplied to inputs of a multiplexer 42. Control circuit 25 also includes an A/D converter 43 which converts the output signals from multiplexer 42 to digital form, a waveform shaping circuit 44 which executes waveform shaping of the output signal from the crank angle sensor 34 to produce TDC (top dead center) signal pulses as output, and a counter 45 which counts a number of clock pulses (produced from a clock pulse generating circuit which is not shown in the drawings) during each interval between successive TDC pulses from the waveform shaping circuit 44. Control circuit 25 further includes a drive circuit 46a for driving the injector 35, a pattern display drive circuit 46b for driving a pattern display unit 38, a CPU (central processing unit) 47 for performing digital computation in accordance with a program, with a ROM (read-only memory) 48 having various processing programs and data stored therein, and a RAM (random access memory) 49. The A/D converters 39, 40 and 43, multiplexer 42, counter 45, drive circuits 46a, 46b, CPU 47, ROM 48 and RAM 49 are mutually interconnected by an input/output bus 50. The TDC signal is supplied from the waveform shaping circuit 44 to the CPU 47. The control circuit 25 also includes a heater current supply circuit 51, which can for example include a switching element which is responsive to a heater current supply command from CPU 47 for applying a voltage between the terminals of heater element 20, to thereby supply heater current and produce heating of heater element 20.

The voltage $V_S$ developed between electrodes 17a and 17b of the sensor cell element 19, transferred from A/D converter 39, data representing a pump current value $I_P$ corresponding to the current flow through the oxygen pump element 18, transferred from A/D converter 40, together with data representing a degree of throttle valve opening $\theta_{TH}$, data representing the absolute pressure $P_{BA}$ within the intake pipe, and data representing the cooling water temperature $T_W$ respectively selected and transferred by A/D converter 43, are supplied to CPU 47 over the I/O bus 50. In addition a count value from counter 45, which is attained during each period of the TDC pulses, is also supplied to CPU 47 over I/O bus 50. The CPU 47 executes read-in of each of these data in accordance with a processing program which is stored in the ROM 48, and computes a fuel injection time interval $T_{OUT}$ for injector 35 on the basis of the data, in accordance with a fuel injection quantity for engine 2 which is determined from predetermined equations. This computation is performed by means of a fuel supply routine, which is executed in synchronism with the TDC signal. The injector 35 is then actuated by drive circuit 46a for the duration of the fuel injection time interval $T_{OUT}$, to supply fuel to the engine.

The fuel injection time interval $T_{OUT}$ can be obtained for example from the following equation:

$$T_{OUT} = T_I \times K_{O2} \times K_{WOT} \times K_{TW} \quad \ldots (1)$$

In the above equation, $T_I$ is the basic supply quantity, which is determined in accordance with the engine speed of rotation $N_e$ and the absolute pressure $P_{BA}$ in the intake pipe which expresses a basic injection time interval. $K_{O2}$ is a feedback compensation coefficient for the air/fuel ratio, which is set in accordance with the output signal level from the oxygen concentration sensor. $K_{WOT}$ is a fuel quantity increment compensation coefficient, which is applied when the engine is operating under high load. $K_{TW}$ is a cooling water temperature coefficient. $T_I$, $K_{O2}$, $K_{WOT}$ and $K_{TW}$ are respectively set by a subroutine of the fuel supply routine.

When the supply of pump current to the oxygen pump element begins, if the air/fuel ratio of the mixture which is supplied to engine 2 at that time is in the lean region, then the voltage which is produced between electrodes 17a and 17b of the sensor cell element 19 will be lower than the output voltage from the reference voltage source 22, and as a result the output voltage level from the differential amplifier 21 will be positive. This positive voltage is applied through the series-connected combination of resistor 23 and oxygen pump element 18. A pump current thereby flows from electrode 16a to electrode 16b of the oxygen pump element 18, so that the oxygen within the gas holding chamber 13 becomes ionized by electrode 16b, and flows through the interior of oxygen pump element 18 from electrode 16b, to be ejected from electrode 16a as gaseous oxygen. Oxygen is thereby drawn out of the interior of the gas holding chamber 13.

As a result of this withdrawal of oxygen from the gas holding chamber 13, a difference in oxygen concentration will arise between the exhaust gas within the gas holding chamber 13 and the atmospheric air within the atmospheric reference chamber 15. A voltage $V_S$ is thereby produced between electrodes 17a and 17b of the sensor cell element 19 at a level determined by this difference in oxygen concentration, and the voltage $V_S$ is applied to the inverting input terminal of differential amplifier 21. The output voltage from differential amplifier 21 is proportional to the voltage difference between the voltage $V_S$ and the voltage produced from reference voltage source 22, and hence the pump current is proportional to the oxygen concentration within the exhaust gas. The pump current value is output as a value of voltage appearing between the terminals of current sensing resistor 23.

When the air/fuel ratio is within the rich region, the voltage $V_S$ will be higher than the output voltage from reference voltage source 22, and hence the output voltage from differential amplifier 21 will be inverted from the positive to the negative level. In response to this negative level of output voltage, the pump current which flows between electrodes 16a and 16b of the oxygen pump element 18 is reduced, and the direction of current flow is reversed. Thus, since the direction of flow of the pump current is now from the electrode 16b to electrode 16a, oxygen will be ionized by electrode 16a, so that oxygen will be transferred as ions through oxygen pump element 18 to electrode 16b, to be emitted as gaseous oxygen within the gas holding chamber 13. In this way, oxygen is drawn into the gas holding chamber 13. The supply of pump current is thereby controlled such as to maintain the oxygen concentration within the gas holding chamber 13 at a constant value, by drawing oxygen into or out of chamber 13, so that the pump current $I_P$ will always be proportional to the oxygen concentration in the exhaust gas, both for operation in the lean region and in the rich region of the air/fuel ratio. The value of the feedback compensation coefficient $K_{O2}$ referred to above is established in accordance with the pump current value $I_P$, in a $K_{O2}$ computation subroutine. This subroutine can for example be similar to a program which is described in U.S. Pat. No. 4,566,419. Specifically, the oxygen concentration refreshing value $V_{O2}$, determined in accordance with $I_P$, is compared with a target air/fuel ratio $V_{ref}$ (which is determined in accordance with the engine parameters), and if $V_{O2} < V_{ref}$, the computation $K_{O2} - \Delta$ is executed, while if $V_{O2} > V_{ref}$, the computation $K_{O2} + \Delta$ is executed.

Figure 4A:
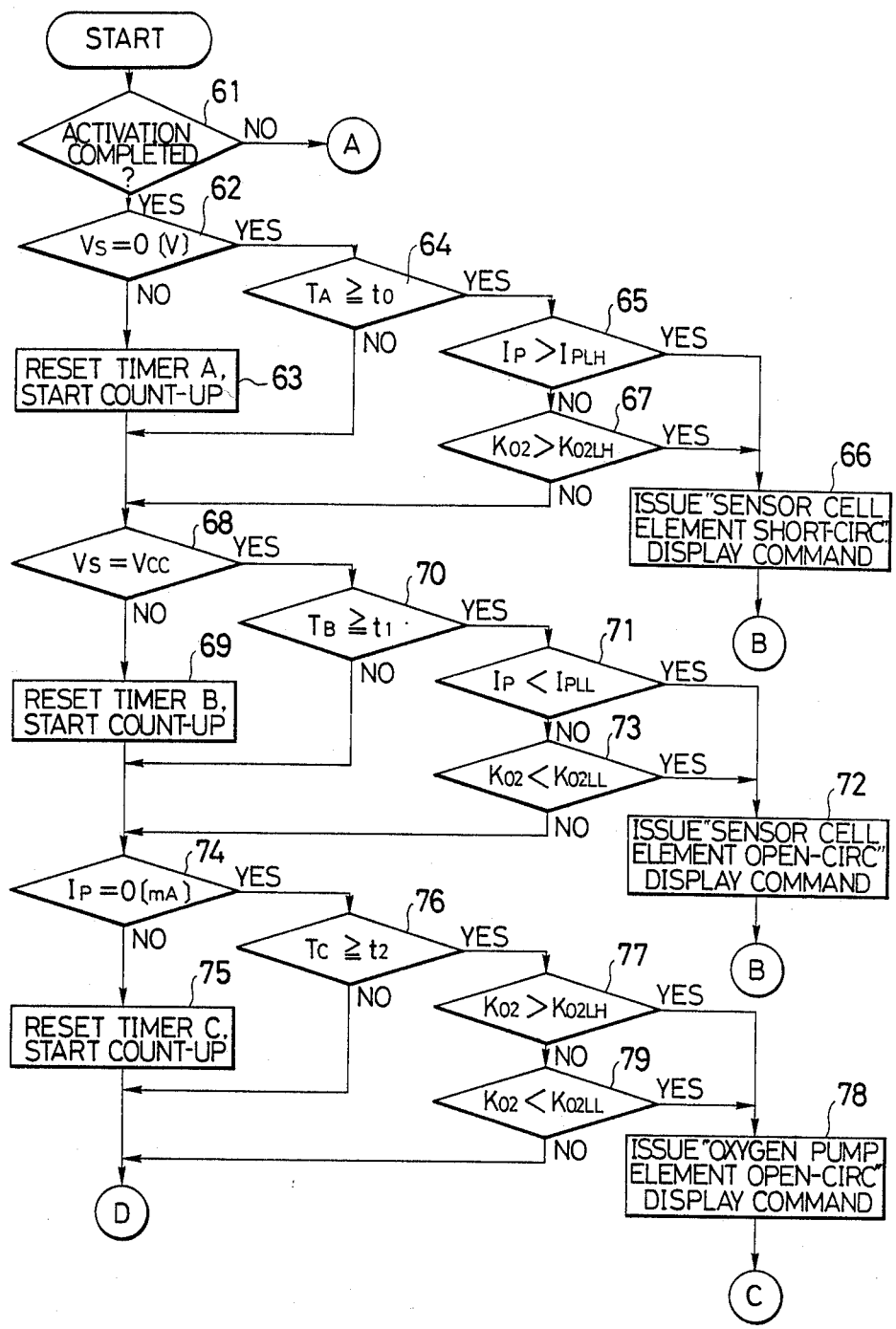
FIGS. 4a, 4b, 4ba and 4bb are flow charts for assistance in describing the operation of a CPU.
Figure 4B:
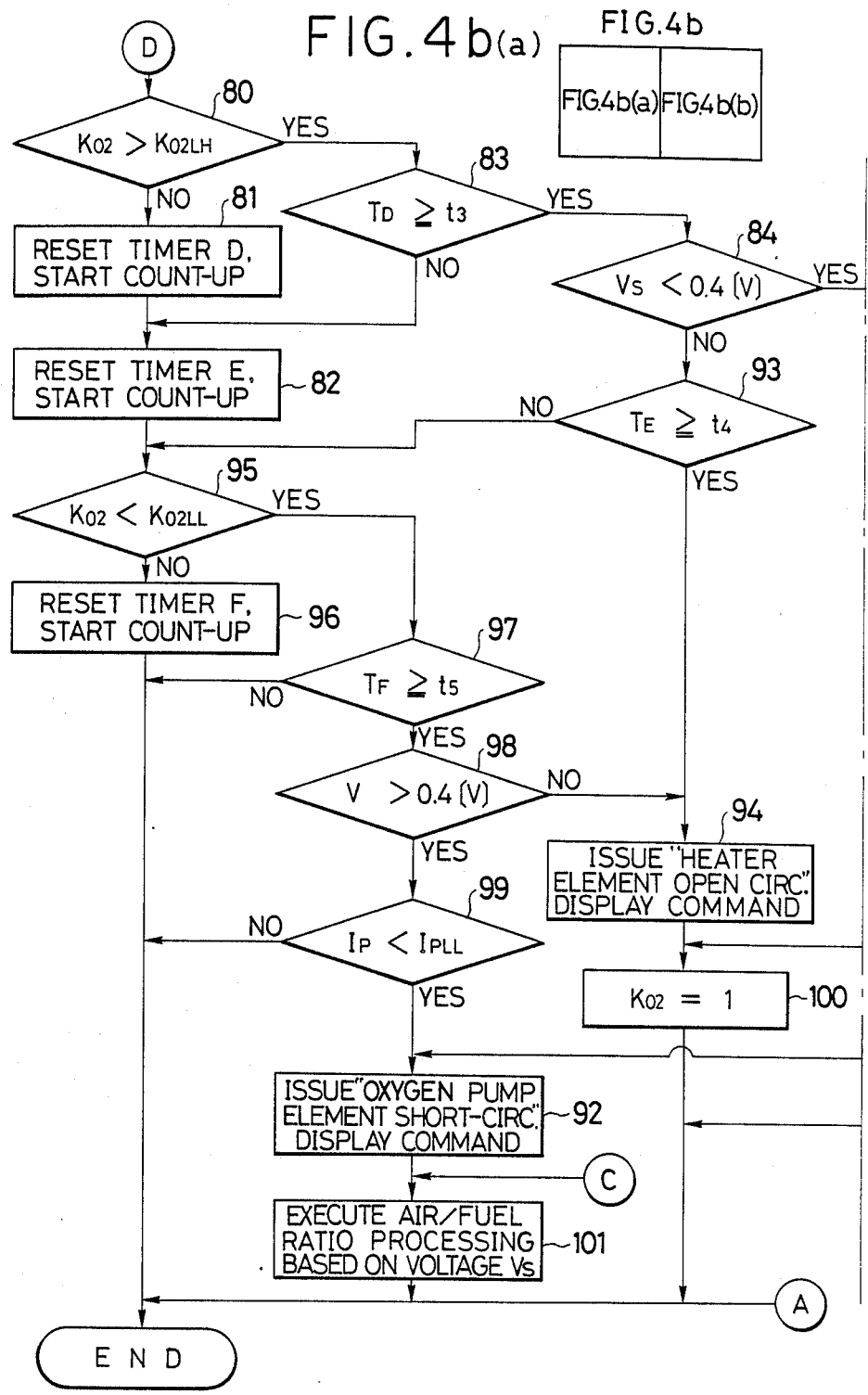
Figure 4B:
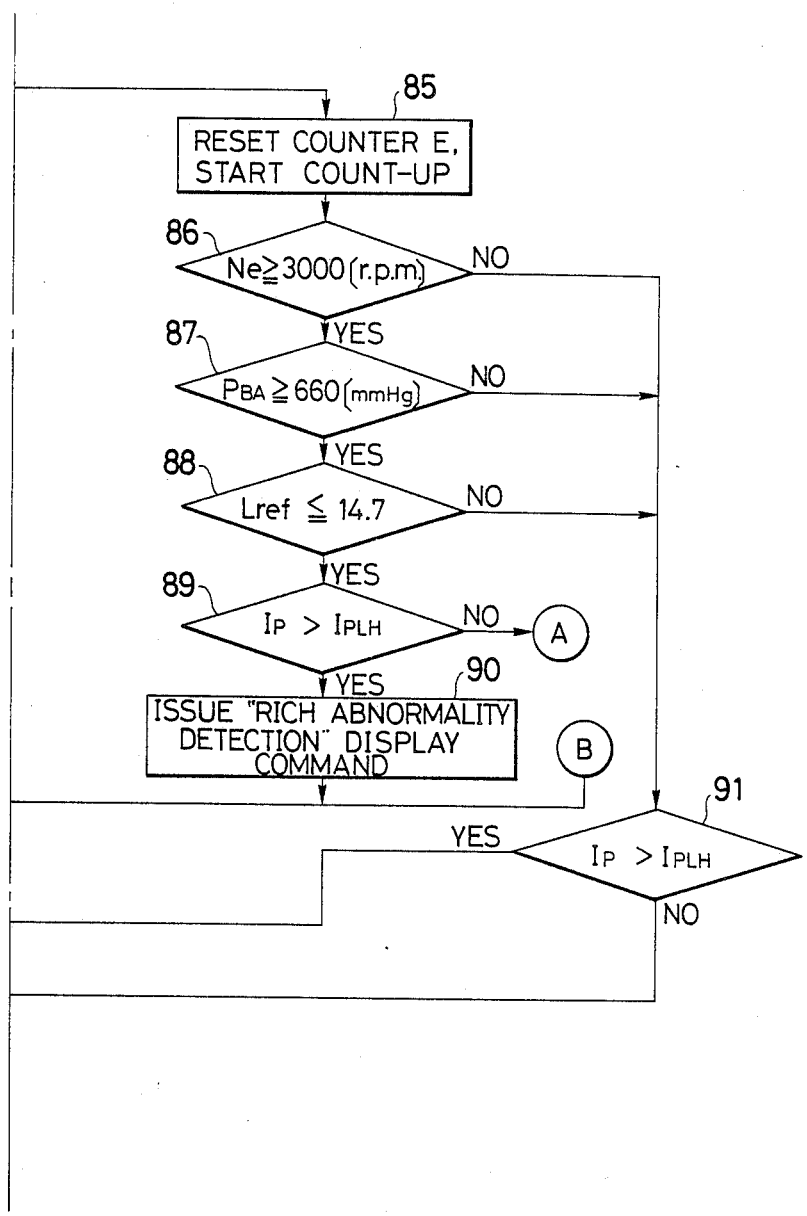

An operating sequence for the oxygen concentration sensor abnormality detection method of the present invention will now be described, referring to the operating flow of CPU 47 shown in FIGS. 4a and 4b. This abnormality detection function is provided as an abnormality detection subroutine of the fuel supply routine, and therefore is executed each time the fuel supply routine is executed.

In the operating sequence, CPU 47 first judges whether or not activation of the oxygen concentration sensor has been completed (step 61). This decision can be based for example upon whether or not a predetermined time duration has elapsed since the supply of heater current to the heater element 20 was initiated. If activation of the oxygen concentration sensor has been completed, the voltage $V_S$ between electrodes 17a and 17b of sensor cell element 19 is read in, and a decision is made as to whether or not $V_S$ is 0 [V] (step 62). If $V_S \neq 0$ [V], then a timer A (not shown in the drawings) in CPU 47 is reset, to begin counting up from zero. If on the other hand $V_S = 0$ [V], then a decision is made as to whether or not a count value $T_A$ of timer A is greater than a time interval $t_0$ (step 64). If $T_A \leq t_0$, then the pump current value $I_P$ is read in, and a decision is made as to whether or not $I_P$ is higher than an upper limit value $I_{PLH}$ (step 65). If $I_P > I_{PLH}$, then since an excessively high value of pump current is flowing while a condition of $V_S = 0$ (V) is continuously maintained, this is taken as indicating a short-circuit between electrodes 17a and 17b of the sensor cell element 19. A "sensor cell element short-circuit" display command is therefore issued to drive circuit 46b (step 66). If $I_P \leq I_{PLH}$, then a decision is made as to whether or not the value of the feedback compensation coefficient $K_{O2}$, computed by a $K_{O2}$ computation subroutine, is higher than an upper limit value $K_{O2LH}$ (step 67). If $K_{O2} > K_{O2LH}$, then this indicates a condition in which $V_S$ is continuously maintained at 0 (V) while an excessively high value of pump current flows in the positive direction, and the feedback compensation coefficient $K_{O2}$ is excessively high. This condition is taken as indicating a short-circuit between electrodes 17a and 17b of the sensor cell element 19, and a "sensor cell element short-circuit" display command is therefore issued to drive circuit 46b (step 66).

After reset of timer A, if it is judged that the count value $T_A$ of timer A has not yet attained time $t_o$, or if it is judged that $K_{O2} \leq K_{O2LH}$, then a decision is made as to whether or not voltage $V_S$ is equal to Vcc (step 68). If $V_S \neq$ Vcc (where Vcc is the circuit power source voltage), a timer B (not shown in the drawings) in CPU 47 is reset and counting up from zero by counter B is initiated (step 69). If on the other hand $V_S = $ Vcc, then a decision is made as to whether or not the count value $T_B$ of timer B is greater than a time $t_1$ (step 70). If $T_B \geq t_l$, then the value of pump current $I_P$ is read in, and a decision is made as to whether or not $I_P$ is smaller than a lower limit value $I_{PLL}$ (step 71). If $I_P < I_{PLL}$, then since a condition of $V_S = $ Vcc is continuously maintained while an excessive level of pump current flow in the negative direction is occurring, this condition is taken as indicating an open-circuit in the connecting leads of electrodes 17a and 17b of the sensor cell element 19, and therefore a "sensor cell element open-circuit" display command is issued to drive circuit 46b (step 72). If $I_P \geq I_{PLL}$, then a decision is made as to whether or not the feedback compensation coefficient $K_{O2}$ (computed in the $K_{O2}$ computation subroutine) is smaller than the lower limit value $K_{O2LL}$ (step 73). If $K_{O2} < K_{O2LL}$, then this shows that although an excessively high level of pump current does not flow, a condition of $V_S = $ Vcc is continuing and the feedback compensation coefficient $K_{O2}$ is excessively small. This is taken to indicate an open-circuit in the connecting leads of electrodes 17a, 17b of sensor cell element 19, and a "sensor cell element open-circuit" display command is issued to drive circuit 46b (step 72).

After timer B has been reset, if it is judged that the count value $T_B$ does not yet correspond to the time value $t_l$, or if it is judged that $K_{O2} \geq K_{O2LL}$, then a decision is made as to whether or not the pump current value $I_P$ is 0 (mA) (step 74). If $I_P \neq 0$ (mA), then a timer C (not shown in the drawings) in CPU 47 is reset and begins counting up from zero (step 75). If on the other hand $I_P = 0$ (mA), then a decision is made as to whether or not the count value $T_C$ of timer C is greater than the time $t_2$ (step 76). If $T_C \geq t_2$, then a decision is made as to whether or not the feedback compensation coefficient $K_{O2}$ is greater than the upper limit value $K_{O2LH}$ (step 77). If $K_{O2} > K_{O2LH}$, then this is taken to indicate an open-circuit in the connecting leads of electrodes 16a, 16b of oxygen pump element 18 while the air/fuel ratio is more rich than the target air/fuel ratio, whereby a condition of $I_P = 0$ (mA) is being continued, so that the feedback compensation coefficient $K_{O2}$ is excessively high. An "oxygen pump element open-circuit" display command is therefore issued to drive circuit 46b (step 78). If $K_{O2} < K_{O2LH}$, then a decision is made as to whether or not the feedback compensation coefficient $K_{O2}$ is smaller than the lower limit value $K_{O2LL}$ (step 79). If $K_{O2} > K_{O2LL}$, then this is taken to indicate that a condition of $I_P = 0$ (mA) is continuously established while the feedback compensation coefficient $K_{O2}$ is excessively low due to an open-circuit in the connecting leads of connecting leads 16a, 16b of the oxygen pump element 18, so that the air/fuel ratio is more lean than the target air/fuel ratio. An "oxygen pump element open-circuit" display command is therefore issued to drive circuit 46b (step 78).

After timer C has been reset, if it is judged that the count value $T_C$ does not yet correspond to the time value $t_2$, or if it is judged that $K_{O2} \geq K_{O2LL}$, then a decision is made as to whether or not the feedback compensation coefficient $K_{O2}$ is greater than the upper limit value $K_{O2LH}$ (step 80). If $K_{O2} \leq K_{O2LH}$, then timers D and E (neither of which is shown in the drawings) in CPU 47 are respectively reset and begin counting up from zero (steps 81, 82). If on the other hand $K_{O2} > K_{O2LH}$, then a decision is made as to whether or not the count value $T_D$ of timer D is greater than a time interval $t_3$ (step 83). If $T_D < t_3$, then timer E is reset and counting up by timer E from zero is initiated (step 82). If $T_D \leq t_3$, then since it is unusual for an operating condition in which the air/fuel ratio is excessively lean to continue for more than time $t_3$, a decision is made as to whether or not the voltage $V_S$ between electrodes 17a and 17b of sensor cell element 19 is lower than 0.4 (V) (step 84) If $V_S < 0.4$ (V), this indicates that the air/fuel ratio is lean as a result of the value of $V_S$. Counter E is then reset and counting up by timer E from zero is initiated (step 85). The engine speed of rotation $N_e$ and the absolute pressure $P_{BA}$ in the intake pipe are then read in, and a decision is made as to whether or not the speed of rotation $N_e$ is greater than 3,000 (r.p.m.). In addition, a decision is made as to whether or not the absolute pressure $P_{BA}$ in the intake pipe is greater than 660 (mm $H_g$) (steps 86, 87), and a decision is made as to whether or not the target air/fuel ratio $L_{ref}$ is set at a value lower than 14.7 (step 88). The target air/fuel ratio may be determined in accordance with engine parameters representing engine load, such as $N_e$ and $P_{BA}$, by reading out a data map. If all of the predetermined conditions $N_e \geq 3,000$ (r.p.m.), $P_{BA} \geq 660$ (mm $H_g$), and $L_{ref} \leq 14.7$ are met, then this is taken to indicate that the engine is operating under a condition of high load with a rich air/fuel ratio. In this case, a decision is made as to whether or not the pump current $I_P$ is higher than the upper limit value $I_{PLH}$ (step 89). If $I_P > I_{PLH}$, then this shows that an excessively high level of pump current is flowing in the positive direction, in spite of the fact that the air/fuel ratio is rich, and therefore this is taken to indicate that gas from the exhaust has leaked into the atmospheric reference chamber 15 due to a reason such as a crack in the solid electrolytic member 11, so that the voltage $V_S$ is lower than 0.4 (V). This is a "rich abnormality" detection condition, and a "rich abnormality detection" display command is issued to drive circuit 46b (step 90). If at least one of the conditions $N_e \geq 3,000$ (r.p.m.), $P_{BA} \geq 660$ (mm $H_g$), and $L_{ref} \leq 14.7$ is not satisfied, then a decision is made as to whether or not the pump current $I_P$ is greater than the lower limit $I_{PLH}$ (step 91). If $I_P > I_{PLH}$, then this indicates that although the feedback compensation coefficient $K_{O2}$ has been held continuously higher than the upper limit value $K_{O2LH}$, to compensate for a condition of lean air/fuel ratio, and the air/fuel ratio has been thereby made rich, an excessively high level of pump current is flowing in the positive direction. This is taken to indicate that a short-circuit exists between electrodes 16a, 16b of the oxygen pump element 18, and therefore an "oxygen pump element short-circuit" display command is issued to drive circuit 46b (step 92). The target air/fuel ratio $L_{ref}$ is set in accordance with the engine speed of rotation $N_e$ and the absolute pressure $P_{BA}$ in the intake pipe, in synchronism with the TDC signal, during a subroutine of the fuel supply routine.

If it is judged in step 84 that $V_S \geq 0.4$ (V), then this value of $V_S$ is taken as indicating that the air/fuel ratio is rich. Therefore, since it is unusual for the feedback compensation coefficient $K_{O2}$ to exceed the upper limit value $K_{O2LH}$, a decision is made as to whether or not the count value $T_E$ of timer E has exceeded a time interval $t_4$ (step 93). If $T_E > t_4$, then this is taken to indicate that there is an open-circuit in the connecting leads of the heater element 20, or within heater element 20 itself, and a "heater element open-circuit" display command is issued to drive circuit 46b (step 94).

After resetting timer E in step 82 or if it is judged that the count value $T_E$ has not yet attained time $t_4$, a decision is made as to whether or not the feedback compensation coefficient $K_{O2}$ is lower than the lower limit value $K_{O2LL}$ (step 95). If $K_{O2} \geq K_{O2LL}$, then a timer F (not shown in the drawings) within CPU 47 is reset, and begins counting up from zero (step 96). If $K_{O2} < K_{O2LL}$, then a decision is made as to whether or not the count value $T_F$ of timer F is greater than a time interval $t_5$ (step 97). If $T_F \geq t_5$, then a decision is made as to whether or not the voltage $V_S$ between electrodes 17a, 17b of sensor cell element 19 is greater than 0.4 (V) (step 98). If $V_S \leq 0.4$ (V), then since such a value of $V_S$ indicates that the air/fuel ratio is lean, and since it is unusual for the feedback compensation coefficient $K_{O2}$ to fall below the lower limit value $K_{O2LL}$, this condition is taken to indicate that there is an open-circuit in the connecting leads of heater element 20 or within heater element 20 itself, and a "heater element open-circuit" display command is issued to drive circuit 46b (step 94). If on the other hand $V_S > 0.4$ (V), a decision is made as to whether or not the pump current $I_P$ is smaller than the lower limit value $I_{PLL}$ (step 99). If $I_P < I_{PLL}$, then this indicates that in spite of the fact that the feedback compensation coefficient $K_{O2}$ has been continuously held lower than the lower limit value $K_{O2LL}$ to compensate for a condition of rich air/fuel ratio, so that the air/fuel ratio has been made lean, an excessively high level of pump current is flowing in the negative direction. This is taken to indicate that there is a short-circuit between electrodes 16a and 16b of the oxygen pump element 18, and therefore an "oxygen pump element short-circuit" display command is issued to drive circuit 46b (step 92).

If a "sensor cell element short-circuit" display command, a "sensor cell element open-circuit" display command, or a "heater element open-circuit" display command has been issued, then the feedback compensation coefficient $K_{O2}$ is made equal to 1, in order to halt air/fuel ratio feedback control operation (step 100). If an "oxygen pump element short-circuit" display command or an "oxygen pump element open-circuit" display command has been issued, then, operating under the assumption that the sensor cell element 19 is functioning normally, processing is executed to compute the feedback compensation coefficient on the basis of judgment of the air/fuel ratio in accordance with the value of voltage $V_S$ developed between electrodes 17a and 17b of sensor cell element 19 (step 101).

When drive circuit 46b is supplied with any of the display commands described above, a predetermined display pattern is produced upon a display unit 38, in accordance with the contents of the command.

Each of the timers A through F can be implemented by supplying clock pulses to vary the contents of registers within CPU 47.

In the embodiment of the present invention described above, the fuel supply quantity is controlled in accordance with a pump current value $I_P$. However the present invention is not limited to such an arrangement, and it would be equally applicable to a method of abnormality detection for an oxygen concentration sensor of an air/fuel ratio control apparatus which employs a secondary air intake technique, whereby a quantity of secondary intake air could be controlled in accordance with the pump current $I_P$.

Furthermore in the embodiment of the present invention described above, the lead-in aperture 14 is utilized as a gas diffusion control means. However it is also possible to employ a porous material such as alumina ($Al_2O_3$), formed as a porous body which fills a lead-in aperture or the gas holding chamber.

In this way, a system of abnormality detection for an oxygen concentration sensor according to the present invention utilizes the fact that, if an abnormality occurs such as an open-circuit or a short-circuit in electrode connecting leads of an oxygen pump element, then the pump current will be stopped or an excessively high current will flow between the electrodes of the oxygen pump element. Thus, an air/fuel ratio compensation value, such as $K_{O2}$ described above, derived in accordance with an oxygen concentration detection value for use in controlling the air/fuel ratio of a mixture supplied to an engine such as to hold that air/fuel ratio at a target value, will become excessively high or excessively low. Based on this fact, an abnormality in the electrode connection system of the electrodes of the sensor cell element can be reliably detected by the method of the present invention on the basis of the level of voltage which is developed between the electrodes of the sensor cell element, and the level of current which flows between the electrodes of the oxygen pump element, or on the basis of the voltage developed between the electrodes of the sensor cell element, and the air/fuel ratio compensation value. Thus, when an abnormality is detected by the method of the present invention, if air/fuel ratio control in accordance with data from the oxygen concentration sensor is immediately halted, then operation of the engine under a condition of reduced accuracy of control of the air/fuel ratio of the mixture which is supplied to the engine can be prevented. In this way, the invention enables deterioration of exhaust gas pollution cleansing performance to be effectively prevented.

Furthermore, since the level of voltage which is developed between the electrodes of the sensor cell element will depend upon the oxygen concentration within the gas under measurement, if an abnormality occurs in the electrical connection system of the oxygen pump element but no abnormality has occurred with respect to the sensor cell element, then it is possible to avoid halting of air/fuel ratio feedback control. Specifically, changeover can be executed to air/fuel ratio feedback control in accordance with the voltage which is developed between the electrodes of the sensor cell element. This will enable a better performance to be attained with respect to exhaust gas pollution reduction than is possible if air/fuel ratio feedback control is halted.

What is claimed is:

1. A system for abnormality detection in an air/fuel ratio control apparatus of an internal engine comprising:
   an oxygen concentration sensor including two pairs of electrodes disposed in mutual opposition, each said pair sandwiching an oxygen ion-conductive solid electrolytic member:
   gas diffusion control means for providing an exhaust gas of an internal combustion engine to the vicinity of one electrode of each of said two pairs of electrodes;
   control means for applying a pump voltage, determined in accordance with a voltage difference between a sensor voltage which is produced between a first pair of said two pairs of electrodes and a reference voltage determined between a second pair of said two pairs of electrodes to maintain said sensor voltage at said reference voltage, said control means thereby producing, as an output which represents an oxygen concentration sensing value, a value of pump current which flows between said second pair of electrodes;
   means for deriving an air/fuel ratio compensation value, in accordance with said oxygen concentration sensing value, for controlling an air/fuel ratio of a mixture supplied to said internal combustion engine such as to maintain said air/fuel ratio at a target air/fuel ratio;
   drive means for driving an air/fuel ratio control means of said internal combustion engine in accordance with a corrected air/fuel control value which is obtained by applying compensation to an air/fuel ratio control value in accordance with said air/fuel ratio compensation value; and
   means for detecting an abnormality of an electrical connection system of said second pair of electrodes based upon said pump current and upon said air/fuel ratio compensation value.

2. An abnormality detection system according to claim 1 wherein, when a condition occurs in which said pump current is lower than a first predetermined value and said compensation value is out of a normal region, higher than a second predetermined value and lower than a third predetermined value, said condition is judged to indicate an abnormality of an electrical connection system of said second pair of electrodes.

3. An abnormality detection system according to claim 1, wherein oxygen concentration sensing is performed in accordance with said sensor voltage, in the event that an abnormality of the electrical connection system of said second pair of electrodes is detected.

* * * * *